(12) United States Patent
Shiu

(10) Patent No.: US 6,676,699 B2
(45) Date of Patent: Jan. 13, 2004

(54) STENT GRAFT WITH INTEGRATED VALVE DEVICE AND METHOD

(75) Inventor: Brian Shiu, Sunnyvale, CA (US)

(73) Assignee: Medtronic Ave, Inc, Santa Rosa, CA (US)

(*) Notice: Subject to any disclaimer, the term of this patent is extended or adjusted under 35 U.S.C. 154(b) by 0 days.

(21) Appl. No.: 10/132,934

(22) Filed: Apr. 26, 2002

(65) Prior Publication Data

US 2003/0204243 A1 Oct. 30, 2003

(51) Int. Cl.[7] .................................................. A61F 2/06
(52) U.S. Cl. ..................................... 623/1.24; 623/1.35
(58) Field of Search .............................. 623/1.24, 1.26, 623/1.35, 23.68, 1.16

(56) References Cited

U.S. PATENT DOCUMENTS

| | | | | |
|---|---|---|---|---|
| 4,787,901 A | * | 11/1988 | Baykut ........................ | 623/1.26 |
| 6,241,763 B1 | * | 6/2001 | Drasler et al. ............. | 623/1.24 |
| 6,488,702 B1 | * | 12/2002 | Besselink .................. | 623/1.15 |
| 6,605,112 B1 | * | 8/2003 | Moll et al. ................. | 623/1.24 |
| 2001/0039450 A1 | * | 11/2001 | Pavcnik et al. ............ | 623/1.24 |
| 2002/0049486 A1 | * | 4/2002 | Knudson et al. ............ | 623/1.1 |
| 2002/0128703 A1 | * | 9/2002 | Ravenscroft ................ | 623/1.13 |
| 2002/0177894 A1 | * | 11/2002 | Acosta et al. .............. | 623/1.24 |

* cited by examiner

*Primary Examiner*—Corrine McDermott
*Assistant Examiner*—Thomas J Sweet

(57) ABSTRACT

A bifurcated endoluminal prosthesis is provided that includes a valve or gate in one of the bifurcated branches. The valve or gate prevents flow of blood through the branch when it is closed and permits the flow of blood when it is open. In one variation, the valve comprises a spring member attached to a graft material substantially impermeable to the flow of blood. The spring member holds the graft material over the opening that forms a lumen in the bifurcated portion. The spring member may be flipped from a closed position in which it is initially deployed, to an open position whereby the graft material forms an opening continuous with lumen in the bifurcated portion permitting the flow of blood therethrough. The invention may be used in bifurcated or branched tubular grafts for endoluminal placement within a body lumen, including blood vessels, and for the treatment of abdominal and other aneurysms.

21 Claims, 12 Drawing Sheets

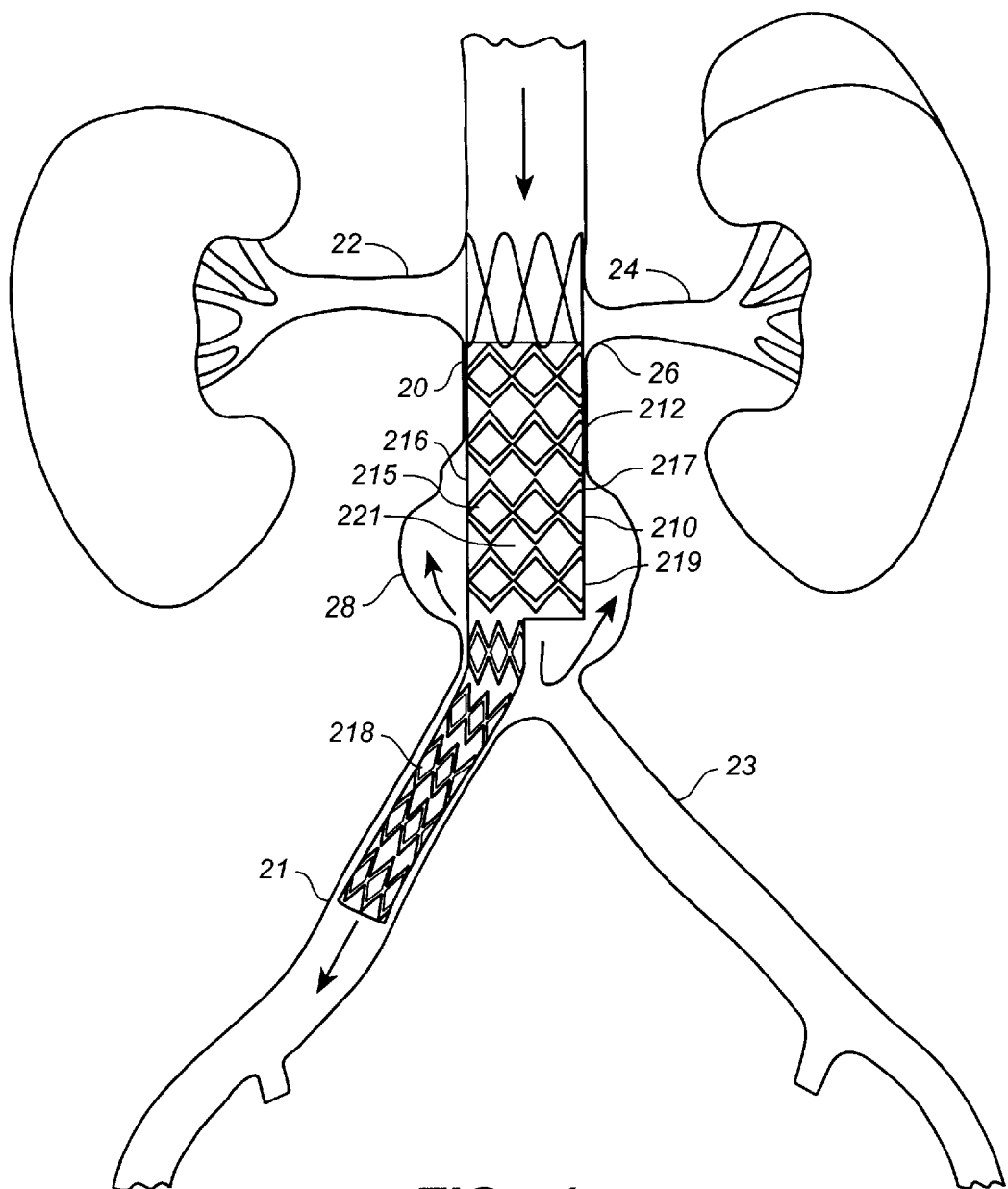
FIG._1
*(PRIOR ART)*

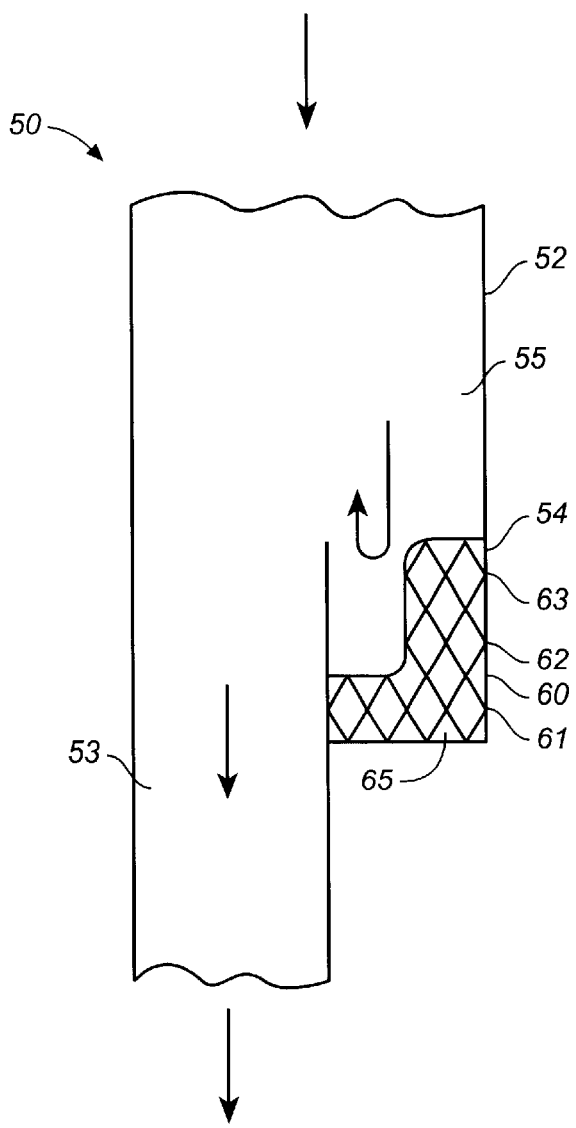
*FIG._2A*
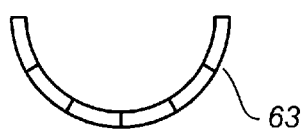
*FIG._2B*
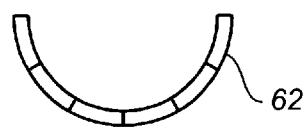
*FIG._2C*
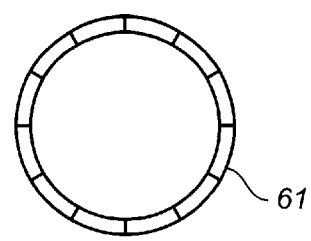
*FIG._2D*

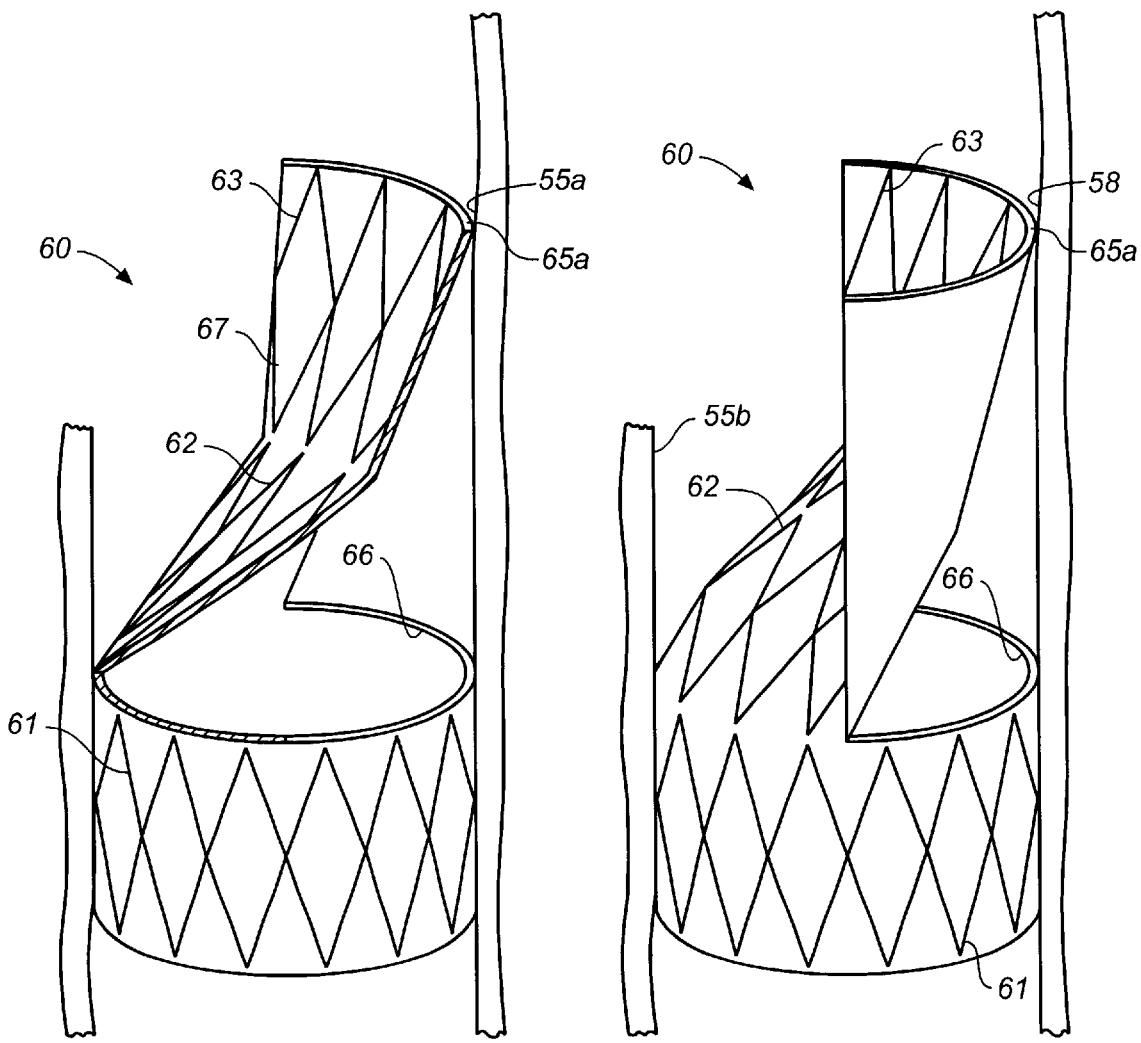
FIG._2E    FIG._2F

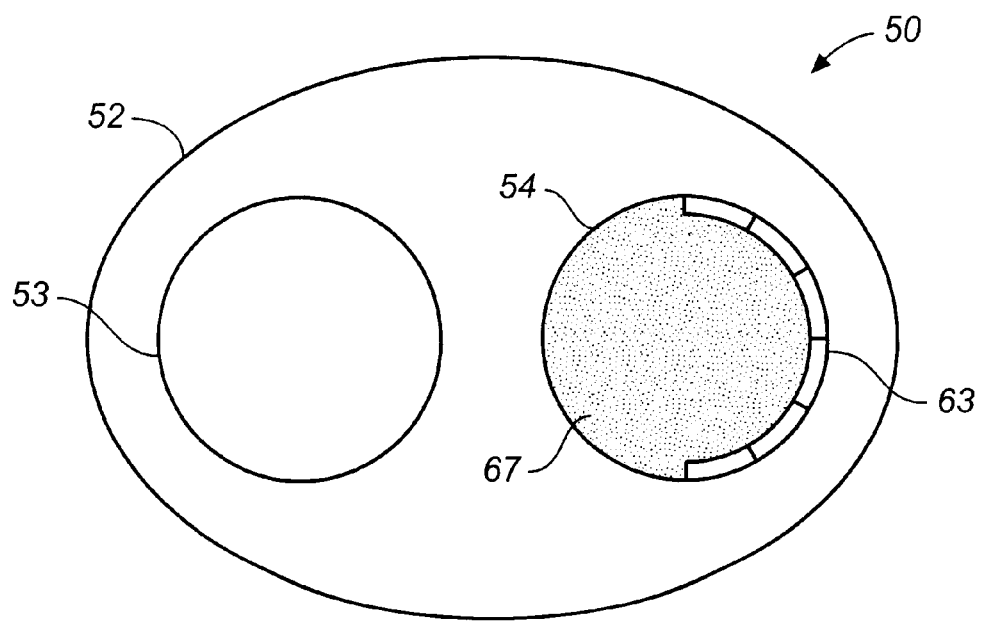
FIG._3
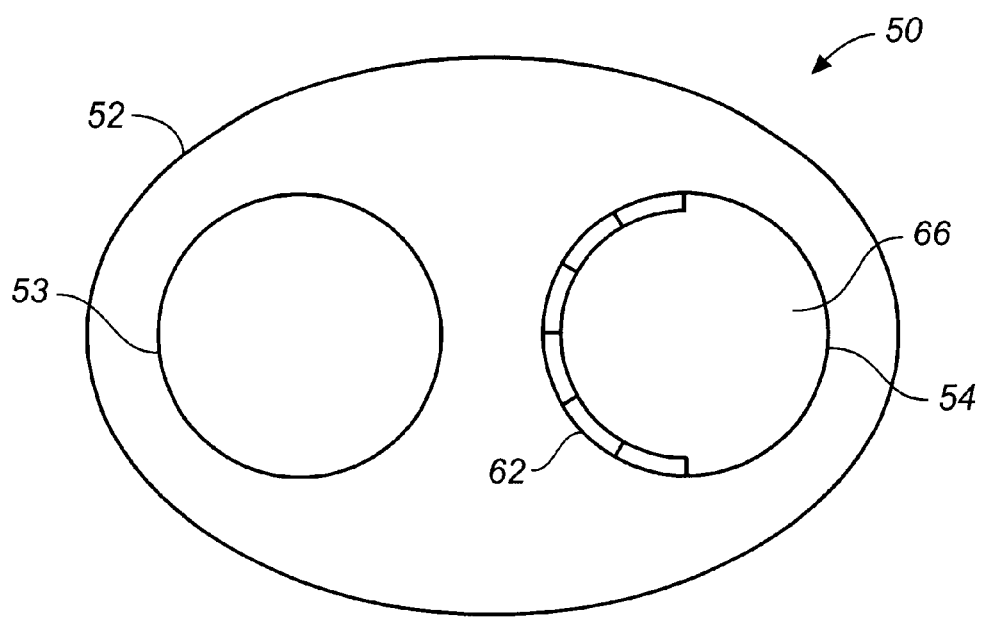
FIG._5

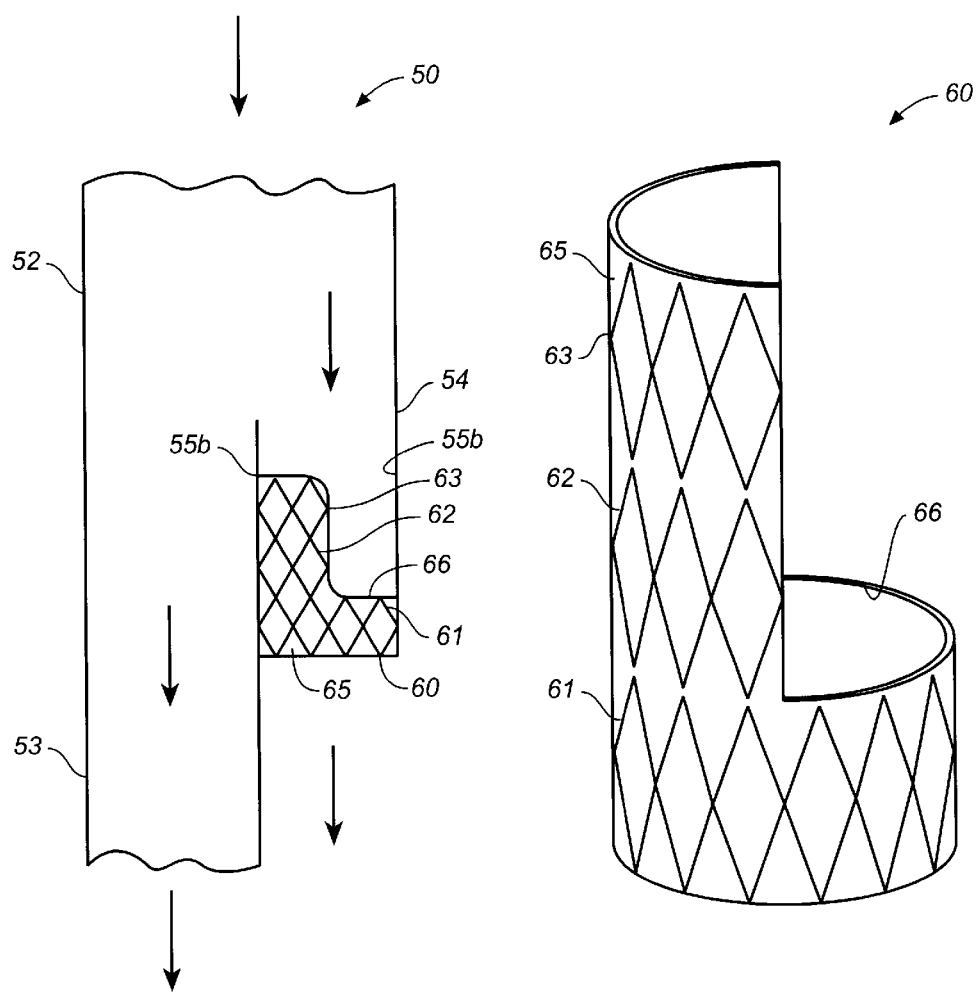
FIG._4A  FIG._4B

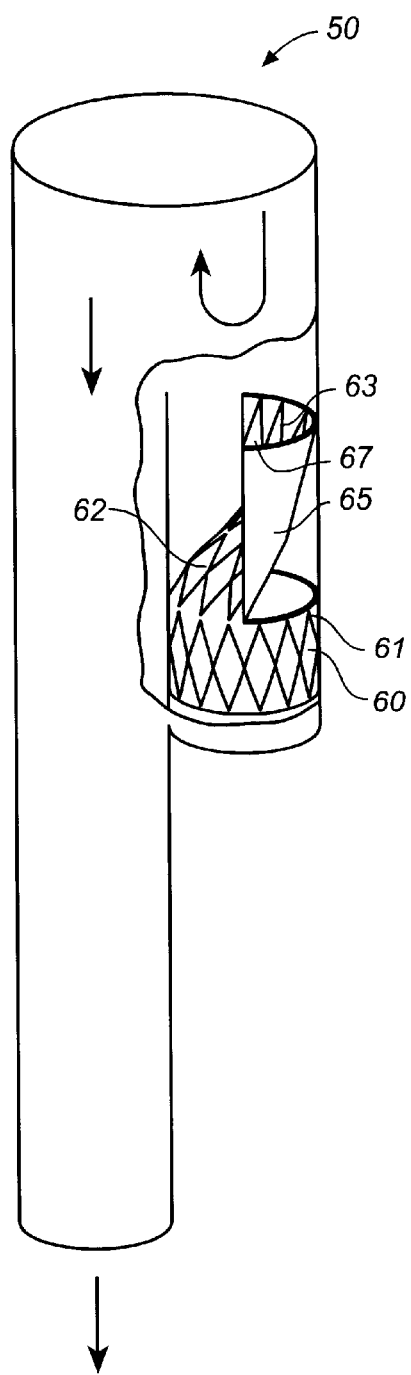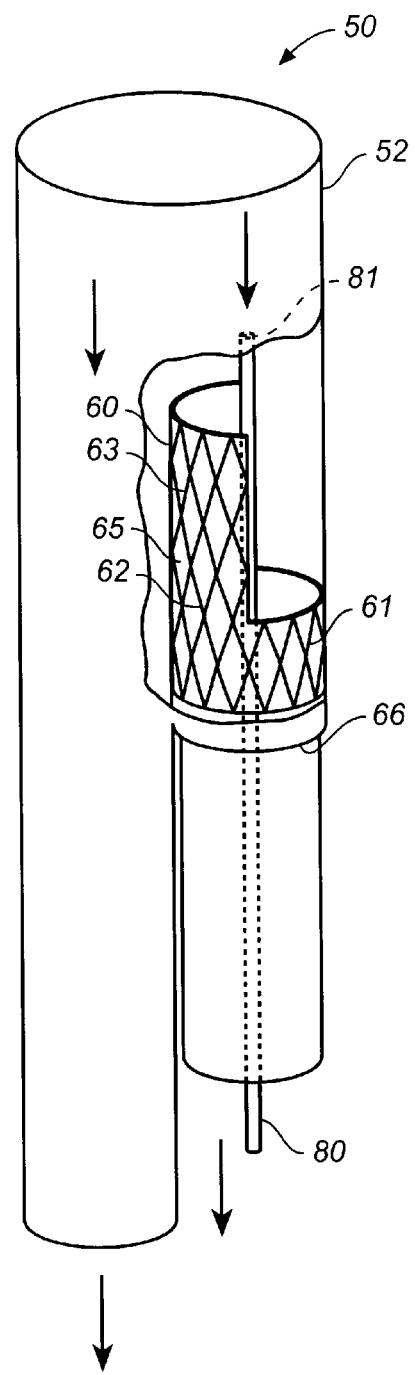
FIG._6   FIG._7

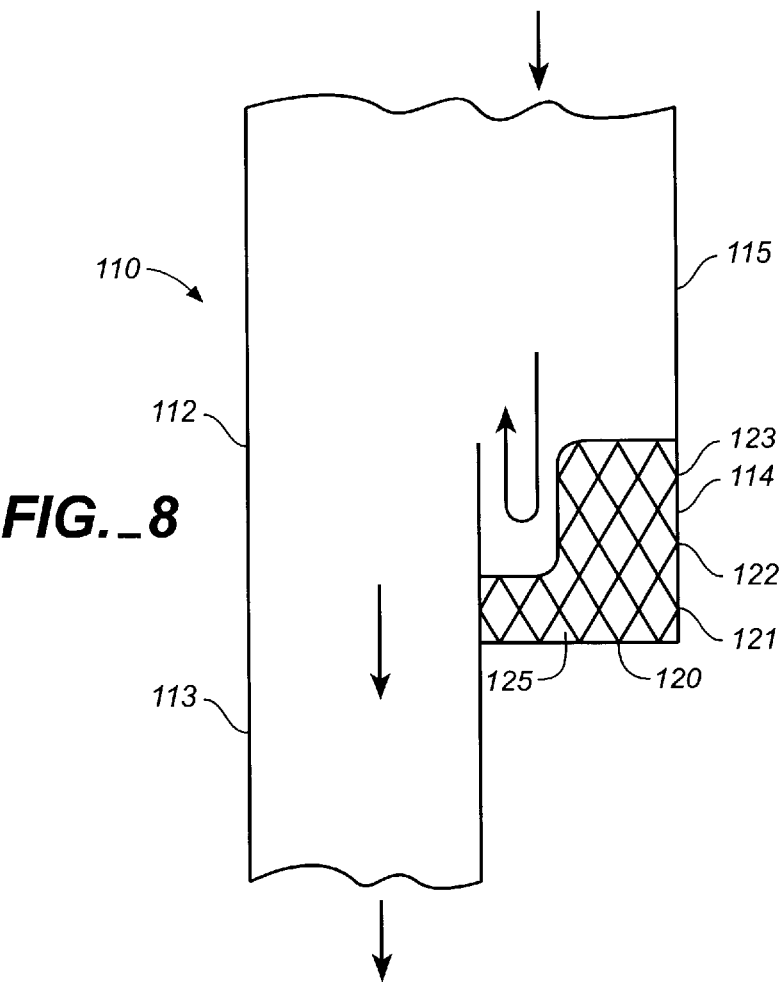
FIG._8
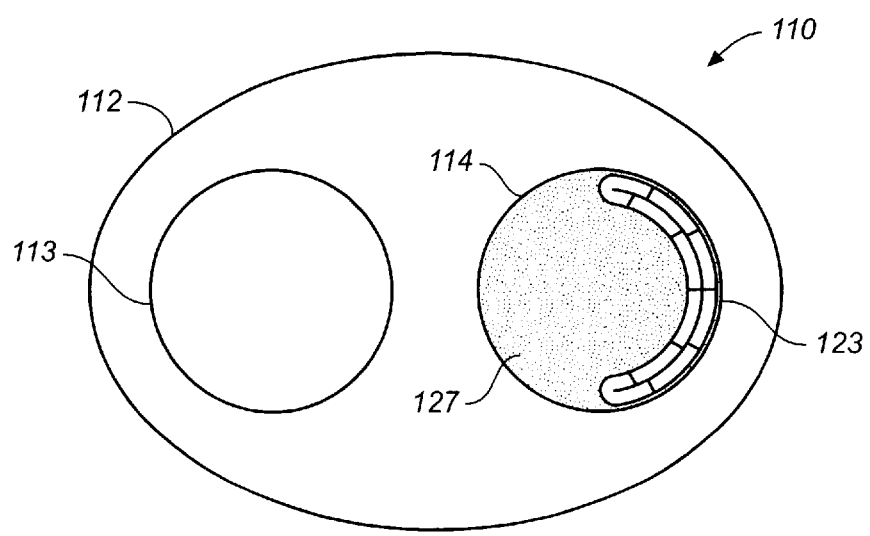
FIG._9A

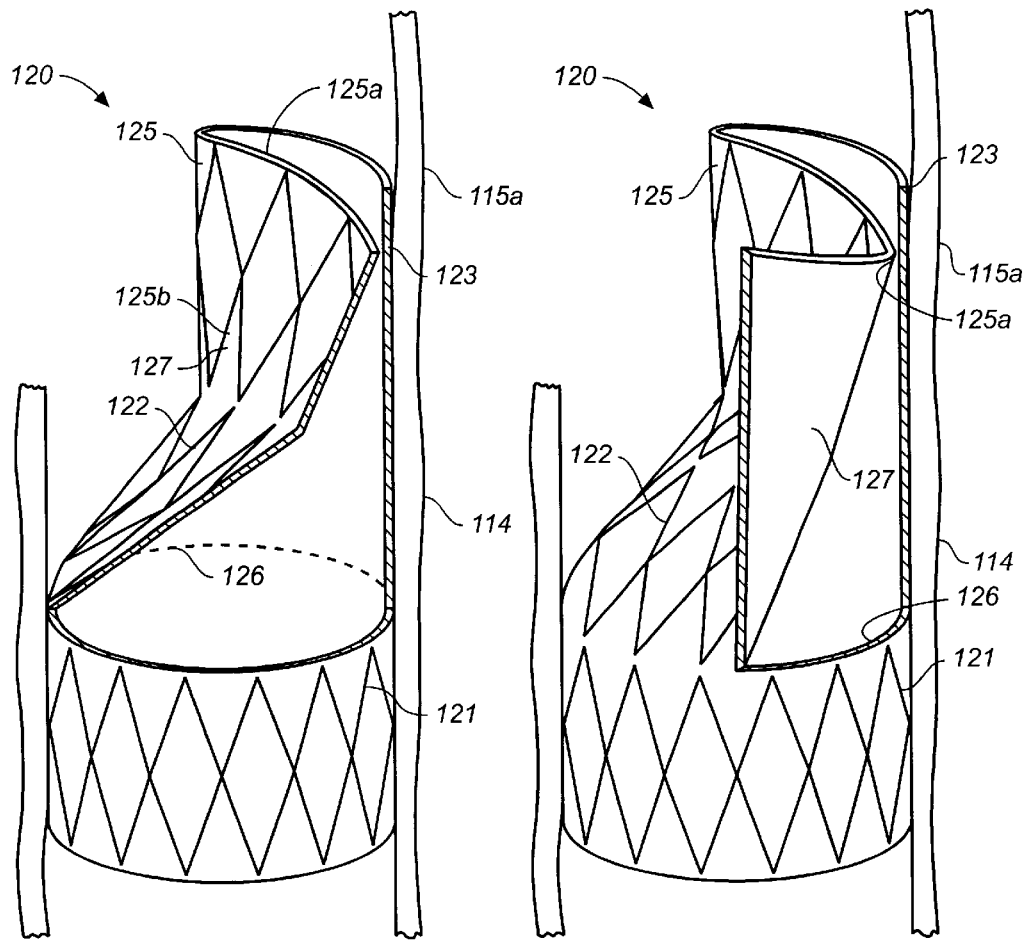
FIG._9B  FIG._9C

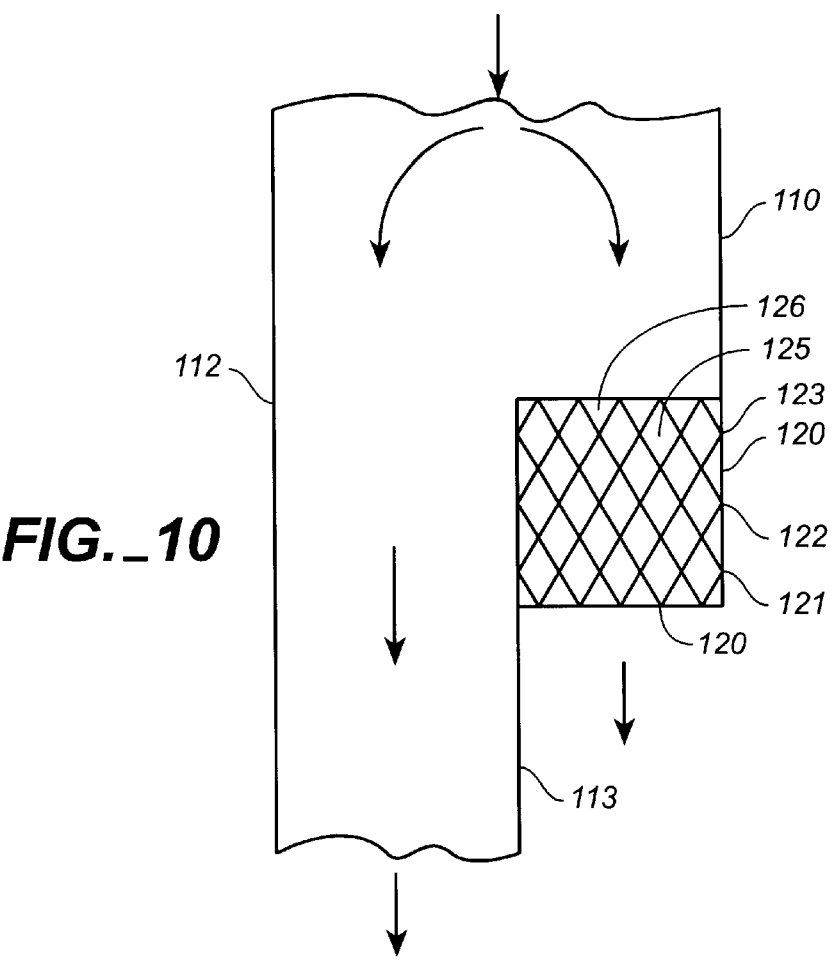
FIG._10
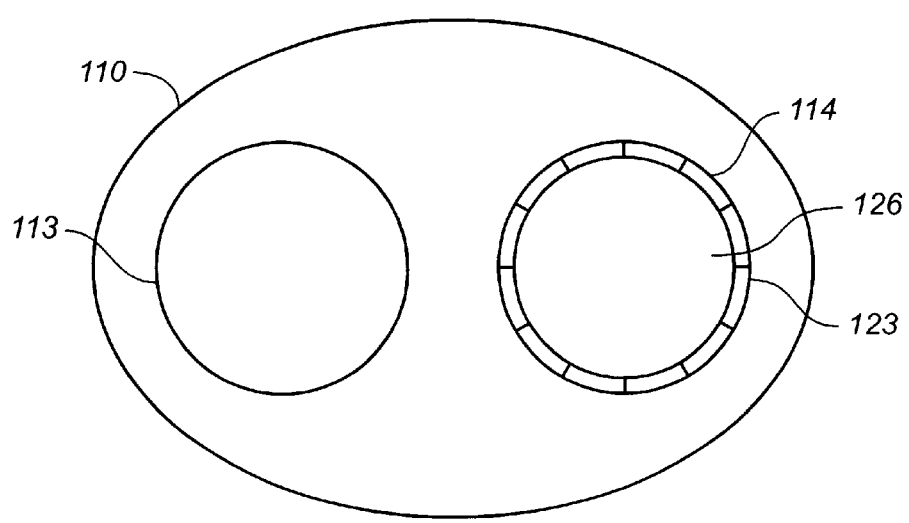
FIG._11A

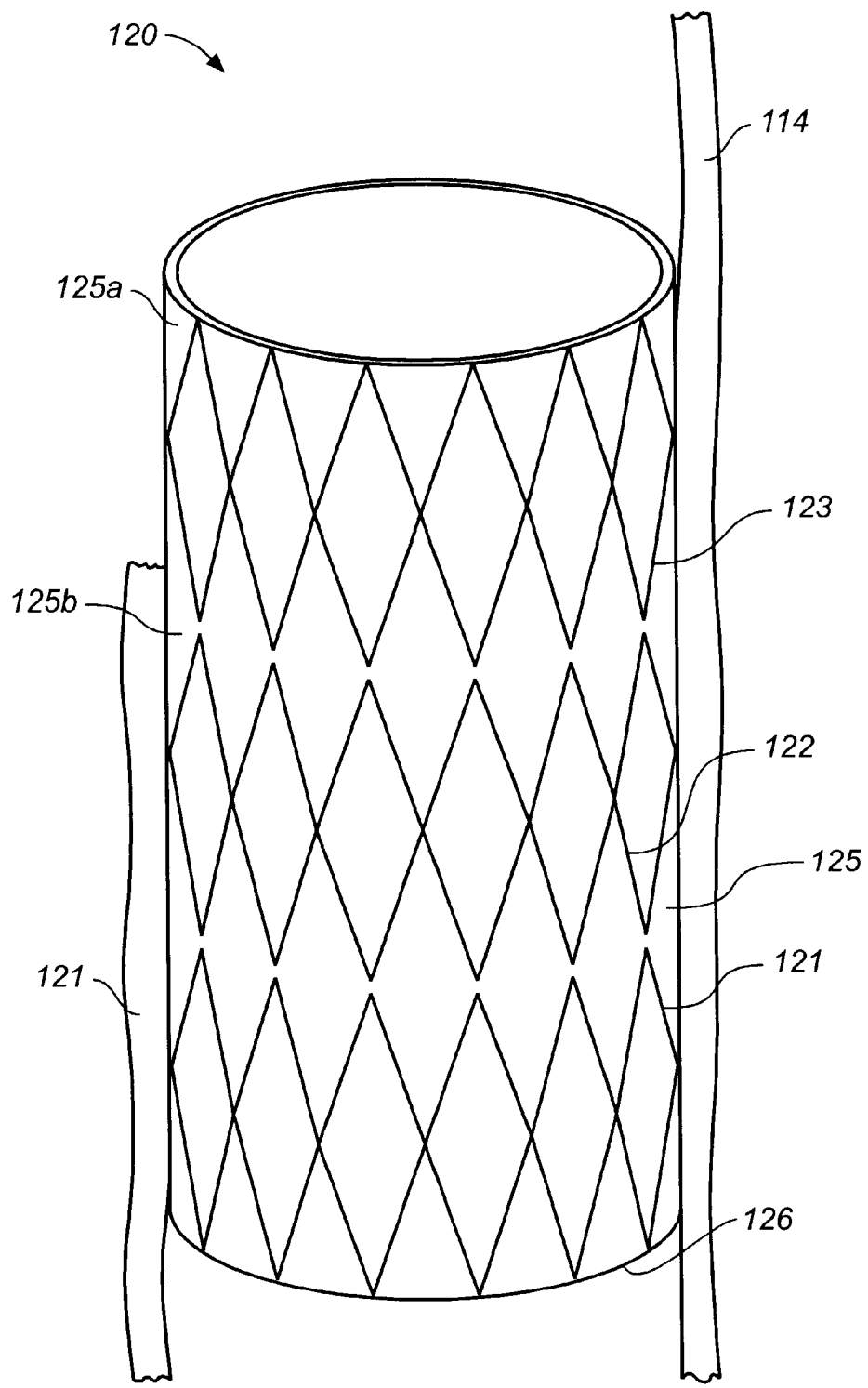
FIG._11B

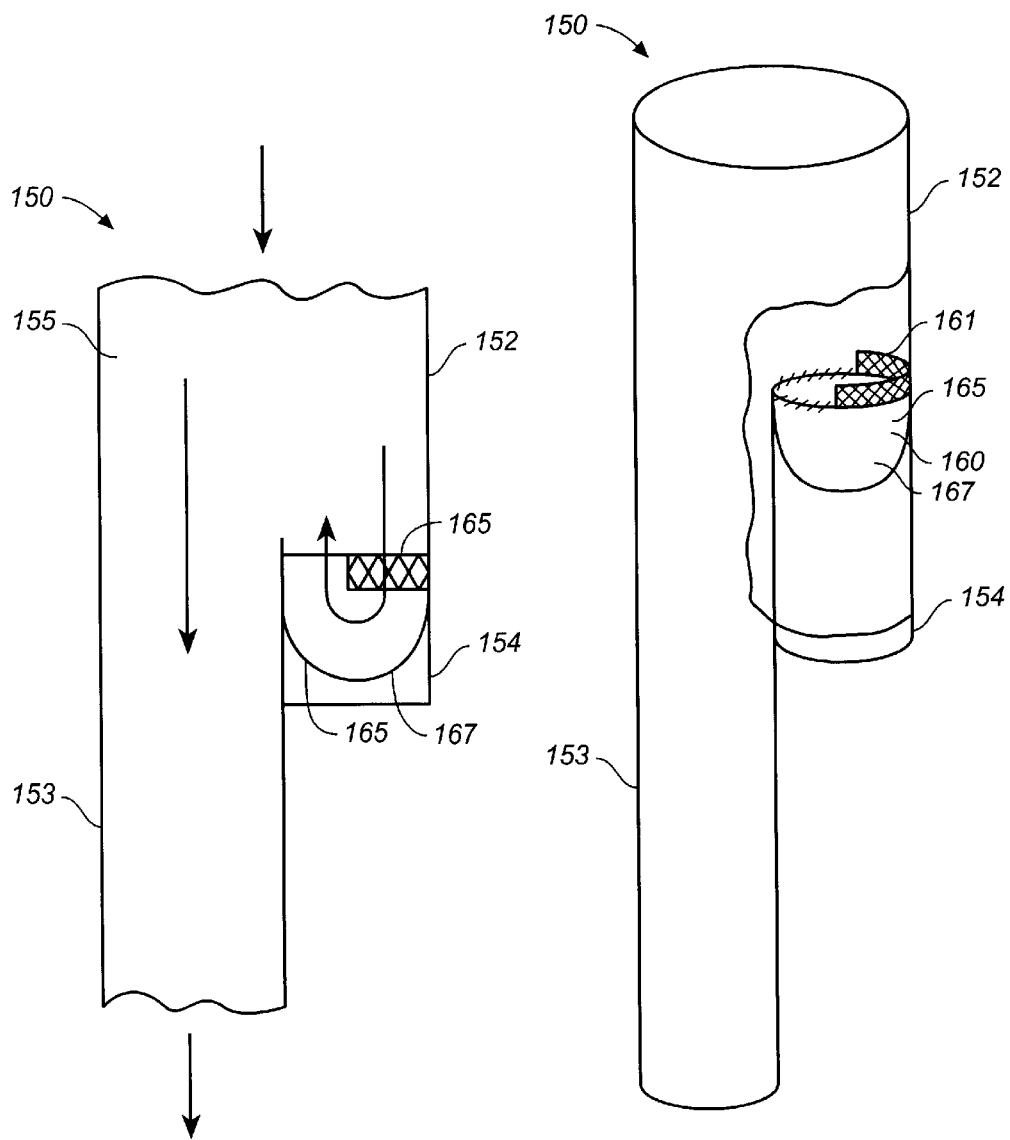
FIG._12  FIG._13

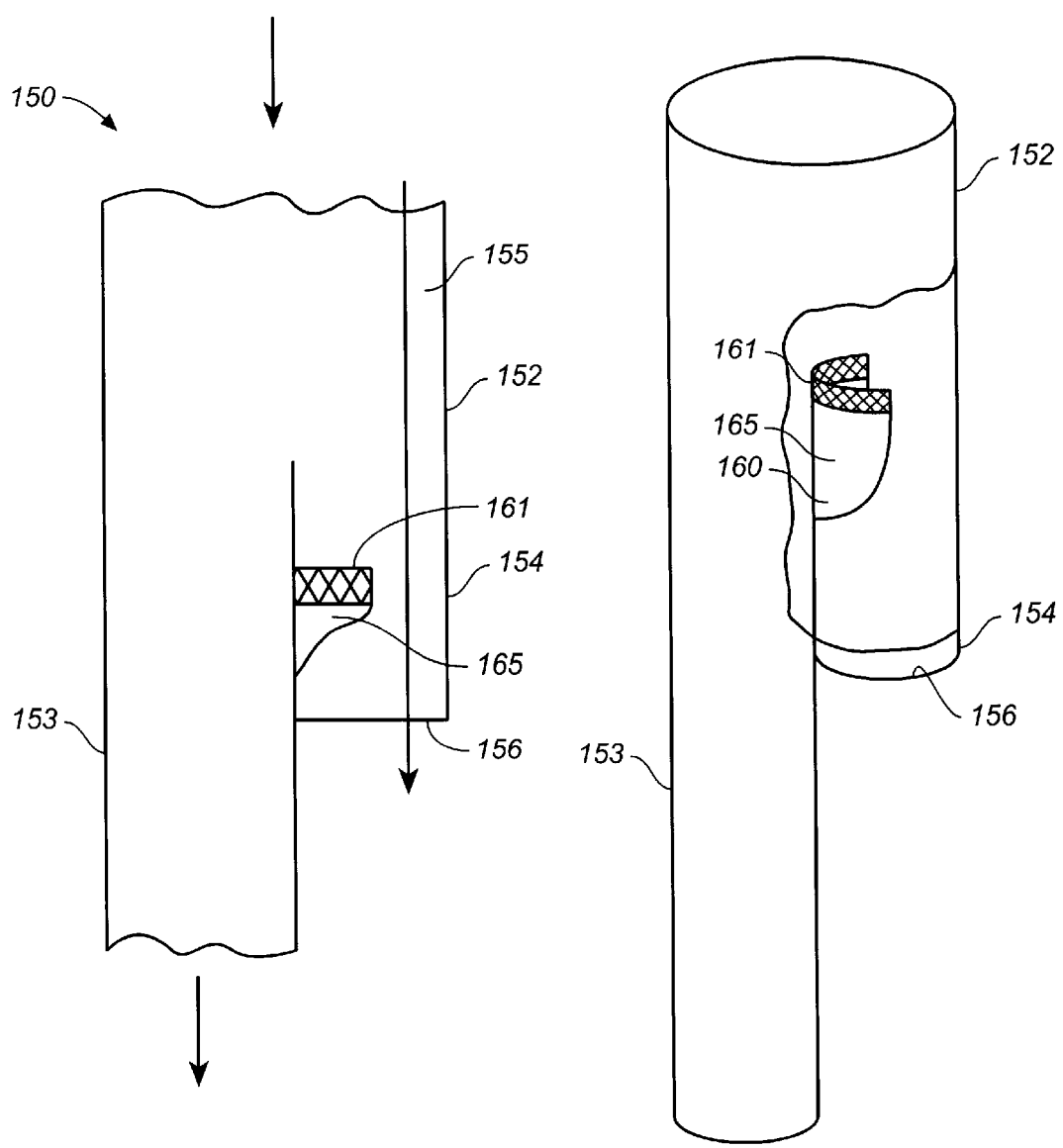
*FIG._14*  *FIG._15*

STENT GRAFT WITH INTEGRATED VALVE DEVICE AND METHOD

FIELD OF THE INVENTION

The present invention relates to tubular prostheses such as grafts and endoluminal prostheses including, for example, stent-grafts and aneurysm exclusion devices, and methods for placement of such grafts and endoluminal structures. Further, the present invention relates to a stent graft and deployment method.

BACKGROUND OF THE INVENTION

A wide range of medical treatments have been previously developed using "endoluminal prostheses," which terms are herein intended to mean medical devices which are adapted for temporary or permanent implantation within a body lumen, including both naturally occurring or artificially made lumens. Examples of lumens in which endoluminal prostheses may be implanted include, without limitation: arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

A number of vascular devices have been developed for replacing, supplementing or excluding portions of blood vessels. These vascular grafts may include but are not limited to endoluminal vascular prostheses and stent grafts, for example, aneurysm exclusion devices such as abdominal aortic aneurysm ("AAA") devices that are used to exclude aneurysms and provide a prosthetic lumen for the flow of blood.

One very significant use for endoluminal or vascular prostheses is in treating aneurysms. Vascular aneurysms are the result of abnormal dilation of a blood vessel, usually resulting from disease or a genetic predisposition, which can weaken the arterial wall and allow it to expand. While aneurysms can occur in any blood vessel, most occur in the aorta and peripheral arteries, with the majority of aneurysms occurring in the abdominal aorta. Typically an abdominal aneurysm will begin below the renal arteries and may extend into one or both of the iliac arteries.

Aneurysms, especially abdominal aortic aneurysms, have been treated in open surgery procedures where the diseased vessel segment is bypassed and repaired with an artificial vascular graft. While considered to be an effective surgical technique in view of the alternative of a fatal ruptured abdominal aortic aneurysm, the open surgical technique suffers from a number of disadvantages. The surgical procedure is complex and requires long hospital stays due to serious complications and long recovery times and has high mortality rates. In order to reduce the mortality rates, complications and duration of hospital stays, less invasive devices and techniques have been developed. The improved devices include tubular prostheses that provide a lumen or lumens for blood flow while excluding blood flow to the aneurysm site. They are introduced into the blood vessel using a catheter in a less or minimally invasive technique. Although frequently referred to as stent-grafts, these devices differ from covered stents in that they are not used to mechanically prop open natural blood vessels. Rather, they are used to secure an artificial lumen in a sealing engagement with the vessel wall without further opening the natural blood vessel that is already abnormally dilated.

Typically these endoluminal prostheses or stent grafts are constructed of graft materials such as woven polymer materials (e.g., Dacron,) or polytetrafluoroethylene ("PTFE") and a support structure. The stent-grafts typically have graft material secured onto the inner diameter or outer diameter of a support structure that supports the graft material and/or holds it in place against a luminal wall. The prostheses are typically secured to a vessel wall above and below the aneurysm site with at least one attached expandable annular spring member that provides sufficient radial force so that the prosthesis engages the inner lumen wall of the body lumen to seal the prosthetic lumen from the aneurysm Abdominal Aortic Aneurysms are frequently treated with bifurcated devices that provide an artificial lumen for flow of blood past the aneurysm and into the iliac vessels that branch off from the aorta. One such commonly used device comprises a bifurcated device having one branch portion longer than the other branch portion. This enables deployment of the main body through one of the iliac arteries where the longer branch is deployed. An extension leg is then deployed through the second iliac artery and is connected with the shorter branch portion.

Iliac vessels associated with abdominal aneurysms frequently have tortuous and twisted anatomies and other structural abnormalities that can prevent effect introduction of an extension leg through an iliac vessel. Often it must be decided prior to deployment whether to use a single lumen prosthesis through one iliac vessel and join the vessels with a shunt further down in the anatomy, or to use a bifurcated prosthesis with an extension. Often a surgeon may not be able to determine the appropriate course of action until the prosthesis is in place or after attempts have been made to deploy an extension graft through a tortuous iliac artery. It would be desirable to provide a device that would enable the decision to be made during the deployment procedure. Devices have been proposed in U.S. Pat. No. 6,102,938, incorporated herein by reference, that provide for sealing off a bifurcated portion of a bifurcated AAA device before or after deployment. Such device is designed for situations where a determination is made during a procedure that it would not be possible to introduce an extension leg into the shorter bifurcated portion to provide blood flow through one of the iliac vessels. It would be desirable to provide an improved or alternative device for accomplishing such task.

Frequently, the AAA procedures are performed in emergency situations where the aorta has ruptured or is extremely fragile and about to rupture. In these situations, frequently a single leg device is deployed through the aorta and one of the iliac vessels occluding the second iliac vessel. This may be done because of the importance of reestablishing blood flow through the aorta and iliac vessel and stopping the loss of blood through the ruptured or rupturing vessel. Such situations may not permit deployment of the second (extension) leg. During this crucial time, in using an existing bifurcated device, blood would be able to flow through the shorter bifurcated portion of the prosthesis into the area of the aneurysm. Accordingly it would be desirable to provide an improved or alternative device that allows for deployment of a bifurcated device in emergency situations that would prevent further blood flow into the area of the aneurysm.

SUMMARY OF THE INVENTION

Accordingly one embodiment according to the present invention provides a novel device and method that include providing a bifurcated device with one leg initially in an occluded position preventing flow of blood through that portion into the aorta. Once the implant is in place and blood is excluded from the aneurysm site, an extension may be introduced and the occluded side opened to blood flow through the extension.

An embodiment of the endoluminal prosthesis comprises a bifurcated tubular member constructed of a graft material and at least one annular support member. The tubular graft is formed of a woven fiber for conducting fluid. The tubular member includes, a proximal opening and distal openings though the bifurcated portions providing a lumen or lumens through which body fluids may flow. When deployed, annular support members support the tubular graft and/or maintain the lumen in a conformed, sealing arrangement with the inner wall of a body lumen. One of the bifurcated portions is provided with a valve that can open or close to permit or prevent the flow of blood through the bifurcated portion. Various embodiments of the valve includes a member that move a section of graft or other material over or away from the opening into the short iliac leg of the bifurcated prosthesis to close or open the short leg to the flow of blood.

The annular support members of an embodiment of the prosthesis each comprise an annular expandable member formed by a series of connected compressible diamond structures. Alternatively, the expandable member may be formed of an undulating or sinusoidal patterned wire ring or other compressible spring member. Preferably the annular support members are radially compressible springs biased in a radially outward direction, which when released, bias the prosthesis into conforming fixed engagement with an interior surface of the vessel. Annular support members are used to create a seal between the prosthesis and the inner wall of a body lumen as well as to support the tubular graft structure. The annular springs are preferably constructed of Nitinol. Examples of such annular support structures are described, for example, in U.S. Pat. Nos. 5,713,917 and 5,824,041 incorporated herein by reference. When used in an aneurysm exclusion device, the support structures have sufficient radial spring force and flexibility to conformingly engage the prosthesis with the body lumen inner wall, to avoid excessive leakage, and prevent pressurization of the aneurysm, i.e., to provide a leak resistant seal. Although some leakage of blood or other body fluid may occur into the aneurysm isolated by the prosthesis, an optimal seal will reduce the chances of aneurysm pressurization and resulting rupture.

The annular support members are attached or mechanically coupled to the graft material along the tubular graft by various means, such as, for example, by stitching onto either the inside or outside of the tubular graft.

An embodiment according to the present invention provides such a tubular graft for endoluminal placement within a blood vessel for the treatment of abdominal and other aneurysms. In this embodiment, the endoluminal prosthesis is an aneurysm exclusion device forming a lumen for the flow of body fluids excluding the flow at the aneurysm site. The aneurysm exclusion device may be used for example, to exclude an aneurysm in the aorta (Abdominal Aortic Aneurysm ("AAA") device) in which the prosthesis is bifurcated.

The generally Y-shaped bifurcated tubular prosthesis has a trunk joining at a graft junction with a pair of lateral limbs, namely an ipsilateral limb and a contralateral limb. In a bifurcated prosthesis, the proximal portion of the prosthesis comprises a trunk with a proximal opening and the distal portion is branched into at least two branches with distal openings. Preferably the ipsilateral limb is longer so that when deployed, it extends into the common iliac. The contralateral limb includes a valve located therein that is initially in a closed position in which body fluids flow from the proximal opening through the distal opening of the ipsalateral limb while the flow of body fluid through the contralateral limb is prevented by the valve. A single limb extension member is provided having a mating portion for coupling with a lateral limb of a bifurcated member and an adjustable length portion extending along an axis from a distal end of the mating portion. The insertion of the limb extension into the contralateral portion of the main prosthesis opens the valve which is then in part maintained open by the extension limb, permitting blood flow from the proximal opening in the main prosthesis through the distal opening in the contralateral and extension limbs.

The valve in one embodiment comprises a plurality of support members coupled to a section of graft material. One of the support members is an annular member forming an opening for the flow of body fluids. A proximal support member is a semicircular member which has an closed position in which the section of graft material forms a cover over the opening formed by the annular member, and an open position in which the section of graft material is held is a position against the wall of the prosthesis so that the opening formed by the annular member is in fluid communication with the flow of body fluid through the prosthesis.

In another embodiment the valve comprises a plurality of annular support members coupled to a section of graft material where at least one of the annular support members is configured to be folded to form a semicircular member engaged to an inner circumference of the bifurcated prosthesis. When the valve is in an open position, the support members are in an open configuration whereby the annular members and a section of graft material form a lumen through which blood may flow. When the valve is in a closed position, one of the annular support members is folded to that the graft material attached to the folded annular member is drawn across the opening through the short leg in which the valve is located.

In another embodiment the valve comprises a graft material sewn in part on an inner circumference of the bifurcated prosthesis and forming a pocket when the valve is closed. A portion of an annular member is sewn on to at least a portion of the section of graft material not sewn on to the prosthesis. When the valve is in a closed position, the annular member holds section of the graft material in a position over the opening in the short leg of the prosthesis. The annular member in this position is across from the location where the opposite side of the section of graft material is sewn on to the prosthesis. When the valve is in a closed position, the annular member holds the pocket formed by the section of graft material closed. The annular member in this position is against the location where the section of graft material is sewn on to the prosthesis so that the opening in the short leg provides a lumen through which blood may flow from the proximal end of the prosthesis to the distal end of the short leg.

The compressed profile of the prosthesis, including the valve, is sufficiently low to allow the endoluminal graft to be placed into the vasculature using a low profile delivery catheter. The prosthesis can be placed within a diseased vessel via deployment means at the location of an aneurysm. Various means for deliver of the device through the vasculature to the site for deployment, are well known in the art and may be found for example is U.S. Pat. Nos. 5,713,917 and 5,824,041. In general, the endoluminal prosthesis is radially compressed and loaded in a catheter for delivery to the deployment site. The aneurysm site is located using an imaging technique such as fluoroscopy and is guided through a femoral iliac artery with the use of a guide wire to the aneurysm site. Once appropriately located, a sheath restraining the tubular graft may be retracted to release the annular springs to expand and attach or engage the tubular member to the inner wall of the body lumen. The iliac extension is also loaded into a catheter and is then located into the main body of the stent graft and within the iliac vessel and is placed through an opened valve where it is deployed. According to an embodiment, when deployed, the iliac has proximal annular springs which when located within the inner lumen of the main body hold or maintain the valve open. The distal portion of the extension extends into one of the iliac vessels.

BRIEF DESCRIPTION OF THE DRAWINGS

FIG. 1 is a side elevational view of an endoluminal prosthesis of the prior art.

FIG. 2A is a side view of a valve in a closed position as positioned in a prosthesis according to an embodiment of the invention.

FIG. 2B is a top cross sectional of a proximal most support member of the valve of FIG. 2A.

FIG. 2C is a top cross sectional of a middle support member of the valve of FIG. 2A.

FIG. 2D is a top cross sectional of a distal most support member of the valve of FIG. 2A.

FIG. 2E is a front cut away view of the valve of FIG. 2A in a closed position.

FIG. 2F is a back cut away view of the valve of FIG. 2A in a closed position.

FIG. 3 is a top view of the prosthesis and valve of FIG. 2A.

FIG. 4A is a side view of a valve of the prosthesis of FIG. 2A in an open position.

FIG. 4B is a side view of the valve of FIG. 4A in an open position.

FIG. 5 is a top view of the prosthesis and valve of FIGS. 4A–4B.

FIG. 6 is a perspective partial cutaway view of the prosthesis of FIG. 2A.

FIG. 7 is perspective partial cutaway view of the prosthesis of FIG. 4A with an extension in place and the valve in an open position.

FIG. 8 is a side view of another embodiment of a valve in a closed position according to the invention.

FIG. 9A is a top view of the prosthesis and valve of FIG. 8.

FIG. 9B is a front cut away view of the valve of FIG. 9A in an open position.

FIG. 9C is a back cut away view of the valve of FIG. 9A in an open position.

FIG. 10 is a side view of a valve of the prosthesis of FIG. 8 in an open position.

FIG. 11A is a top view of the prosthesis and valve of FIG. 10.

FIG. 11B is a side view of the valve of FIG. 11A in an open position.

FIG. 12 is a side view of another embodiment of a valve in a closed position according to the invention.

FIG. 13 is a perspective partial cutaway view of the prosthesis of FIG. 12.

FIG. 14 is a side view of a valve of the prosthesis of FIG. 12 in an open position.

FIG. 15 is perspective partial cutaway view of the prosthesis of FIG. 14.

DETAILED DESCRIPTION

FIG. 1 illustrates a bifurcated prosthesis of the prior art. The prosthesis 210 is shown in place in an abdominal aorta 20. The aorta 20 is joined by renal arteries 22 and 24 at the aorto-renal junction 26. Just below the aorta-renal junction 26 is an aneurysm 28, a diseased region where the vessel wall is weakened and expanded. Below the aneurysm 28, the aorta 20 bifurcates into right and left iliac vessels 21, 23, respectively. The elongated bifurcated tubular prosthesis 210 is deployed at the region of aneurysm 28 for the purpose of relieving blood pressure against the weakened vessel wall, by acting as a fluid conduit through the region of the aneurysm 28. In its deployed condition, a main body portion 216 of the prosthesis 210 defines a conduit for blood flow through the aorta 20 and into the iliac vessel 21. Before deploying an iliac extension (not shown), blood unobstructedly flows through the short iliac portion 219 into the aorta 20 as illustrated.

Annular support members (rings) 212 attached to a tubular graft 25, are designed to exert a radially outward force, sufficient to bias the tubular graft 215 of the endoluminal prosthesis 210 into conforming fixed engagement with the interior surface of aorta 20 above aneurysm 28. The tubular graft 215 provides a leak resistant seal between the prosthesis and the inner wall of the aorta 20. The proximal aortic portion 217 of the prosthesis 210 is located within aorta 20, and the long ipsalateral iliac portion limb 218 is located within the right iliac vessel 21. The short iliac portion 219 is located within the aorta 20. The flow of blood after the main body portion 216 has been deployed is illustrated in FIG. 1.

After deployment of the main body portion 216, a contralateral iliac extension limb (not shown) may be located within left iliac vessel 23, and near the graft junction 221 within the short iliac portion 219. The contralateral iliac extension limb (not shown) may include a proximal support member biasing the extension into conforming fixed engagement with the interior surface of the short iliac portion 219.

To deploy the prosthesis 210, the main body portion 216 of the prosthesis is loaded into a catheter (not shown). The main body is placed in a constrained position within a sheath or cover (not shown) of the catheter and maintains main body 216 in a compressed configuration as it is delivered to the aneurysm site. The main body portion 216 is delivered in a compressed state via catheter through a surgically accessed femoral artery, to the desired deployment site. The cover is retracted when the distal end of the catheter (not shown) is located at the deployment site, releasing the annular members 212 from the compressed position to expand into the deployed position illustrated in FIG. 1.

Using a second catheter (not shown), the contralateral iliac extension limb (not shown) may be separately deployed through a surgically accessed femoral artery and into the short iliac portion 219 after placement of the main body portion 216.

FIGS. 2A–15 illustrate embodiments of the endoluminal prosthesis, delivery systems and methods according to the present invention. The arrows in these figures indicate the flow of blood when deployed in the corresponding configuration, within an aorta of a patient. Although an endoluminal prosthesis, delivery system and method according to the invention may be used in any bifurcated or branched body lumen that conducts body fluid, they are described herein with reference to a bifurcated device used in the treatment of an aortic aneurysm, in particular in the abdomen of a patient.

FIGS. 2A–7 illustrate an embodiment of the invention in which a bifurcated prosthesis 50 includes a main aortic portion 52, which splits into a long iliac portion 53 and a short iliac portion 54. The main aortic portion 52 and the iliac portions 53, 54 define a conduit splitting into two conduits through which blood may flow to bypass an aortic aneurysm. The prosthesis 50 comprises a tubular graft 55 and a series of radially compressible annular support members (not shown but similar to support members 212 described above with reference to FIG. 1) attached to tubular graft 55. The annular support members support the graft and/or bias the prosthesis 50 into conforming fixed engagement with an interior surface of an aorta 20. The annular support members are preferably spring members having predetermined radii and are preferably constructed of a material such as Nitinol in a superelastic, shape set annealed condition. The tubular graft 55 is preferably formed of a biocompatible, low-porosity woven fabric, such as a woven polyester. The graft material is thin-walled so that it may be compressed into a small space, yet capable of acting as a strong, leak-resistant, fluid conduit when in tubular form. In this embodiment, the annular support members are sewn to the outside of the tubular graft 55 material by sutures. Alternative mechanisms of attachment may be used (such as embedding or winding within material, adhesives, staples or other mechanical connectors) and the annular support members may be attached to the inside of the tubular graft 55.

A valve 60 is located adjacent or within the conduit-corresponding to the short iliac portion 54. The valve 60 has an open position (FIGS. 4A–4B, 5 and 7) and a closed position (FIGS. 2A, 2E, 2F, 3 and 6). The valve 60 includes three support members 61, 62, 63 generally formed of attached diamond-like structures. The distal most support member 61 (FIG. 2D) comprises an annular member in which the diamond-like structures are attached in a ring. The support members 62 (FIG. 2C) and 63 (FIG. 2B) comprise cylindrical-wall-like partial rings or semicircular members. The valve 60 may be a separate insert that is held in position within the short iliac portion 54 by the radial force of the support member 61 which may be a spring member formed e.g., of Nitinol against the inside of the short iliac portion 54. Alternatively or in addition, the valve 60 may be attached to the inner wall of the short iliac portion 54 by suturing or other attachment means.

The support members 62, 63 may be flipped (elastically everted) from a first position forming a semicircle with an inner and outer circumference, to a second position in which the side forming the inner circumference in the first position becomes the outer circumference in the second position and the side forming the outer circumference in the first position becomes the inner circumference in the second position (the ends approximately maintaining their position to the inner wall of the short iliac leg). The support members 62, 63 are in the first and closed position in FIGS. 2A, 2E, 2F, 3 and 6 and are in the second and open position in FIGS. 4A–4B, 5 and 7.

The support members 61, 62, 63 are sewn onto a section of graft material 65. The section of graft material 65 is configured to extend around the inner circumference of the annular support member 61 forming a tube around the annular support member 61. The section of graft material 65 is shaped or cut so that it is generally semicircular in shape where it is sewn around the support members 62, 63 to match the shape of those members 62, 63. The section of graft material 65 is located on the inner circumference of the support members 62, 63 when they are in the first, closed position, and, on the outer circumference of the support members 62, 63 when they are in the second, open position.

When in the first and closed position as illustrated in FIGS. 2A, 2E, 2F, 3, and 6, the support member 61 holds the section of graft material 65 in place around the circumference of the lumen in the short iliac portion 54 of the prosthesis 50 where it forms a lumen 66. The support members 62 and 63 hold the section of graft material 65 in a position over the lumen 66 forming a cover 67 (FIG. 3) that prevents the flow of blood through the lumen 66 or the short iliac portion 54. The proximal most support member 63 holds a portion 65a of a section of the graft material 65 against a first portion 55a of an inner circumference of the tubular graft 55. (FIGS. 2E, 2F) The support member 62 located between support members 61 and 63 provides a transition for the section of the graft material 65 across the lumen 66 to provide the cover 67 (FIGS. 2E, 2F).

The support members 62 and 63 are flipped (elastically everted) over into the second, open position as illustrated in FIGS. 4A–4B, 5 and 7. In this position, the graft material 65 surrounding the support members 62, 63 that in the first position formed the cover 67, is held in position against the inner wall (i.e., a second portion 55b of an inner circumference of the tubular graft 55 opposite from the first portion 55a of the inner circumference) of the short iliac portion 54 of the prosthesis 50 so that it does not interfere with the flow of blood through the lumen 66.

In one embodiment the prosthesis 50 is deployed as follows. The valve 60 is initially in a closed position and the prosthesis 50 is loaded into a catheter 80. The prosthesis 50 along with the valve 60 may be radially compressed within a delivery catheter 80. The catheter 80 is located in position to deploy the prosthesis in the abdominal aorta of a patient with an aneurysm in the aorta (not shown) below the aorta-renal junction (not shown). The prosthesis is deployed by retracting a sheath that is holding the prosthesis 50 in its radially compressed position.

Surgical methods and apparatus for accessing the surgical site are generally known in the art and may be used to place the catheter within the vasculature and deliver the prosthesis to the deployment site. Additionally, various actuation mechanisms for retracting sheaths of catheters are known in the art. The prosthesis 50 may be delivered to the deployment site by one of several ways. A surgical cut down may be made to access a femoral iliac artery. The catheter 80 is then inserted into the artery and guided to the aneurysm site using fluoroscopic imaging where the prosthesis 50 is then deployed. The members 51 supporting the graft 55, biased in a radially outward direction, are released to expand and engage the prosthesis 50 in the vessel against the vessel wall to provide an artificial lumen for the flow of blood. Another technique includes percutaneously accessing the blood vessel for catheter delivery, i.e., without a surgical cutdown. An example of such a technique is set forth in U.S. Pat. No. 5,713,917, incorporated herein by reference.

When deployed, the prosthesis 50 is in position with the aortic portion 52 engaging the neck region just below the renal arteries 22, 24. The long iliac portion 53 is located within the iliac vessel 21 while the short iliac portion 54 is within the aorta 20 just proximal of the iliac vessel 23 as illustrated in FIGS. 2A, 3 and 6.

Referring to FIG. 7, a catheter 80 has been inserted through the iliac vessel 23 in a manner that is typically used to deploy an extension graft, and the extension member 68 has been deployed. In inserting the catheter 80, the tip 81 of the catheter 80 is first inserted by guiding it between the inner wall of the short iliac portion 54 and the outer circumference of the support members 62, 63 in their closed position. The tip 81 of the catheter 80 is tapered so that as it is inserted, it flips the support members 62, 63 into the second position, opening the valve 60. The support members 62, 63 demonstrate an over center spring action whereby they are stable in both the closed and open valve positions illustrated in FIGS. 2A–7. Once the support members 62, 63 are moved over a center, they will move to the opposite position.

Once the support member 62, 63 are moved from the closed valve position to the open valve position, the extension member 68 that is loaded in the catheter 80 is released from the catheter 80 in a position in which at least a portion of the extension member 68 is located within the lumen 66 in the open valve 60 and maintains the valve 60 in an open position with the radial force exerted by support members 69 on the extension member 68 (as shown in FIG. 7). The extension member 68 extends into the iliac artery and forms a lumen for the flow of blood therethrough. The support members are constructed of a Nitinol that is preset to maintain a closed configuration so in the absence of an opening force, the valve will close According to this embodiment, the valve 60 is initially in a closed position when the prosthesis 50 is deployed. Thus, flow of blood into the aneurysm through the short iliac portion or leg 54 is prevented until an extension member 68 is placed the second iliac artery 23 and into the short iliac portion 54. The valve 60 thus will remain closed if the surgeon determines that it is not feasible or desirable to deploy an extension member through the iliac vessel 23.

FIGS. 8–11B illustrate another embodiment according to the invention in which a bifurcated prosthesis 110 includes a main aortic portion 112, which splits into a long iliac portion 113 and a short iliac portion 114. The main aortic portion 112 and the iliac portions 113, 114 define a conduit splitting into two conduits through which blood may flow to bypass an aortic aneurysm. The prosthesis 110 comprises a tubular graft 115 and a series of radially compressible annular support members (not shown but similar to support members 212 described above with reference to FIG. 1) attached to tubular graft 115. The annular members support the graft and/or bias the prosthesis 110 into conforming fixed engagement with an interior surface of an aorta (not shown). The annular support members are preferably spring members having predetermined radii and are preferably constructed of a material such as Nitinol in a superelastic, shape set annealed condition. The tubular graft 115 is preferably formed of a biocompatible, low-porosity woven fabric, such as a woven polyester. The graft material is thin-walled so that it may be compressed into a small diameter, yet capable of acting as a strong, leak-resistant, fluid conduit when in tubular form. In this embodiment, the annular support members are sewn on to the outside of the tubular graft 115 material by sutures. Alternative mechanisms of attachment may be used (such as embedding or winding within material, adhesives, staples or other mechanical connectors) and the annular support members may be attached to the inside of the tubular graft 115.

A valve 120 is located adjacent or within the conduit corresponding to the short iliac portion 114. The valve 120 has an open position (FIGS. 10, 11A and 11B) and a closed position (FIGS. 8 and 9A–9C). The valve 120 includes three support members 121, 122 and 123 comprising attached diamond-like structures formed into rings. The valve 120 may be held in position within the short iliac portion 114 by the radial force of the distal most support member 121 which may be a spring member formed e.g., of Nitinol. Alternatively or in addition, the valve 120 may be attached in part to the inner wall of the short iliac portion 114, for example, by suturing or other mechanical means.

The support members 121, 122, 123 are sewn onto section of a graft material 125. The graft material 125 extends around the inner circumference of the annular support members 121, 122, 123 forming at tube around the inner circumference of the annular support members 121, 122, 123.

The support members 122, 123 may be flipped (elastically everted) from a first position in which the support members are folded into semicircular configurations (wherein each ring forming a support member (122, or 123) are folded into two folded halves), to a second position in which the support members 122, 123 are opened into ring configurations. The support members 122, 123 are in the first and closed position in FIGS. 8 and 9A–9C and are in the second and open position in FIGS. 10, 11A and 11B.

When in the first and closed position as illustrated in FIGS. 8, and 9A–9C, the support member 121 holds the section of the graft material 125 in place around the circumference of the lumen in the short iliac portion 114 of the prosthesis 110 where it forms a lumen 126. The support members 122 and 123 are folded so that the outer side of a portion 125b of the section of the graft material 125 is held in a position over the lumen 126, thus forming a cover 127 that prevents the flow of blood through the lumen 126 or the short iliac portion 114. The proximal most support member 123 holds a portion 125a of a section of the graft material 125 against an inner circumference of a portion of the valve 120 that is held against a first portion 115a of the inner circumference of the short iliac portion 114 of the tubular graft 115 (FIGS. 9B, 9C). The support member 122 located between support members 121 and 123 provides a transition for the section of the graft material 125 across the lumen 126 to provide the cover 127 (FIGS. 9B, 9C).

The support members 122 and 123 are flipped over into the second, open position as illustrated in FIGS. 10, 11A and 11B. In this position, the portion 125a of the section of the graft material 125 surrounding the support members 122, 123 that in the first position formed the cover 127, is in tubular configuration, in which the section of the graft material 125 is held against the inner wall of the short iliac portion 114 of the prosthesis 110 so that it does not interfere with the flow of blood through the lumen 126. The prosthesis 120 in the open position, as illustrated in FIG. 11B, extends partially proximally of the inner wall of the graft junction 121 within the short iliac portion 119 that divides the short iliac portion 119 from the long iliac portion 118.

The prosthesis 110 is deployed in a manner similar to the prosthesis 50 described above with reference to FIGS. 2A–7. The valve 120 is initially in a closed position and the prosthesis 110 is loaded into a catheter (not shown). The prosthesis 110 along with the valve 120 may be radially compressed within a delivery catheter and is positioned and deployed in the abdominal aorta of a patient. According to this embodiment, the valve 120 is initially in a closed position when the prosthesis 110 is deployed. Thus, flow of blood into the aneurysm through the short iliac portion or leg 114 is prevented until an extension member (not shown) is placed through the second iliac artery (not shown) and into the short iliac portion 114. The valve 120 thus will remain closed if the surgeon determines that it is not feasible or desirable to deploy an extension member through the iliac vessel.

An extension graft (not shown) is deployed in a manner similar to the deployment of the extension member 68 described above with reference to FIG. 7. Accordingly, the tip of a catheter into onto which the prosthesis 110 is loaded (not shown) is guided between the folded portions 122a, 122b of the support member 122 in its closed configuration, and the folded portions 123a, 123b of the support member 123 in its closed configuration. The tip of the catheter is tapered so that as it is inserted, it opens the support members 122, 123 into the second positions, opening the valve 120. The extension member that is loaded in the catheter is then released from the catheter in a position in which at least a portion of the extension member is located within the lumen 126 in the open valve 120 and maintains the valve 120 in an open position with the radial force exerted by the extension member. The extension member extends into the iliac artery and forms a lumen for the flow of blood therethrough. The support members 122, 123 are constructed of a similar material as support members 61, 62, and 63, described above with reference to FIGS. 2A–7.

FIGS. 12–15 illustrate an embodiment of the invention in which a bifurcated prosthesis 150 includes a main aortic portion 152, which splits into a long iliac portion 153 and a short iliac portion 154. The main aortic portion 152 and the iliac portions 153, 154 define a conduit splitting into two conduits or lumens through which blood may flow to bypass an aortic aneurysm including lumen 156 through the short iliac portion 154. The prosthesis 150 comprises a tubular graft 155 and a series of radially compressible annular support members (not shown, but similar to support members 212 described herein with reference to FIG. 1) attached to tubular graft 155. The annular members 151 support the graft and/or bias the prosthesis 150 into conforming fixed engagement with an interior surface of an aorta. The annular support members are preferably spring members having predetermined radii and are preferably constructed of a material such as Nitinol in a superelastic, shape set annealed condition. The tubular graft 155 is preferably formed of a biocompatible, low-porosity woven fabric, such as a woven polyester the graft material is thin-walled so that it may be compressed into a small diameter, yet capable of acting as a strong, leak-resistant, fluid conduit when in tubular form. In this embodiment, the annular support members are sewn on to the outside of the tubular graft 155 material by sutures. Alternative mechanisms of attachment may be used (such as embedding or winding within material, adhesives, staples or other mechanical connectors) and the annular support members may be attached to the inside of the tubular graft 155.

A valve 160 is located adjacent or within the lumen 156 of the short iliac portion 154. The valve 160 has an open position (FIGS. 14 and 15) and a closed position (FIGS. 12 and 13). The valve 160 comprises a support member 161 sewn onto a section of graft material 165 shaped in the form of a pocket. The support member 161 comprises attached diamond-like structures formed into a semicircular member and is sewn onto the top edge of the pocket-shaped section of graft material 165. The support member 161 is constructed of a similar material as support members 61, 62, and 63, described above with reference to FIGS. 2A–7. The support member 161 has a first position corresponding to the first and closed position of the valve in which the support member is in sealing engagement with a portion of the inner circumference of the tubular graft 155 of the prosthesis 150. The support member 161 has a second position corresponding to the second and open position of the valve 160 where the support member 161 is in sealing engagement with a second portion of an inner circumference of the tubular graft 155, the second portion being on a opposite side of the tubular graft from the first portion. A portion of the section of graft material 165 is secured, e.g., sewn, onto the inner wall of the short iliac portion 154 that forms the lumen 156, i.e. to the second portion of the inner circumference of the tubular graft 155, so that the portion of the section of graft material provides a leak resistant seal with the inner wall of the tubular graft 155. The graft material 165, when the valve 160 is in the first and closed position as illustrated in FIGS. 12, and 13, forms a cover 167 over the lumen 156 in the short iliac portion 154 of the prosthesis 150 that prevents the flow of blood through the lumen 156. The graft material 165 extends around the inner circumference of the annular support members 161 so that graft material 165 and the support structure 161 when in the closed position, form a leak resistant seal with the inner wall of the short iliac portion 154. In addition to attaching the graft 165 to the inner wall of the short iliac portion 154, the valve 160 is held in position within the short iliac portion 154 by the radial force of the support member 161 which may be a spring member formed e.g., of Nitinol. The support member 161 holds the valve 160 in the first and closed position in FIGS. 12 and 13 and in the second and open position in FIGS. 14 and 15.

The support member 161 may be flipped from a first position in which the valve 160 is closed, to a second position in which the valve 160 is open. In the first position, the support member forms a semicircle with an inner and outer circumference. When it is in its second position, the side forming the inner circumference in the first position becomes the outer circumference in the second position and the side forming the outer circumference in the first position becomes the inner circumference in the second position. When the support member 161 is flipped over into the second, open position as illustrated in FIGS. 14 and 15 the graft material 165 surrounding the support member 161 that in the first position formed the cover 167, and the graft material 165 that is attached to the inner wall of the short iliac portion 154, is held by the support member 161 against the inner wall of the short iliac portion 154 of the prosthesis 150 so that it does not interfere with the flow of blood through the lumen 156. The graft material 165 is located on the inner circumference of the support member 161 when it is in the first, closed position, and, on the outer circumference of the support member 161 when it is in 21 the second open position.

The prosthesis 150 is deployed in a manner similar to the prosthesis 50 described above with reference to FIGS. 2A–7. The valve 160 is initially in a closed position and the prosthesis 150 is loaded into a catheter (not shown). The prosthesis 150 along with the valve 160 may be radially compressed within a delivery catheter and is positioned and deployed in the abdominal aorta of a patient. Thus, flow of blood into the aneurysm through the short iliac portion or leg 154 is prevented until an extension member (not shown) is placed through the second iliac artery (not shown) and into the short iliac portion 154. The valve 160 thus will remain closed if the surgeon determines that it is not feasible or desirable to deploy an extension member through the iliac artery.

An extension graft (not shown) is deployed in a manner similar to the deployment of the extension member 68 described above with reference to FIG. 7. Accordingly, the tip of a catheter into onto which the prosthesis 150 is loaded (not shown) is guided between the inner wall of the short iliac portion 154 and the outer circumference of the support member 161 in its closed position. The tip of the catheter is tapered so that as it is inserted, it flips the support member 161 into the second position whereby the support member 161 holds the graft material 165 in a position against the inner wall of the short iliac portion so that the valve 160 is open and the graft material 165 does not obstruct the flow of blood through the short iliac portion 154. The extension member that is loaded in the catheter is then released from the catheter in a position in which at least a portion of the extension member is located adjacent the support member 161 and maintains the valve 160 in an open position with the radial force exerted by the extension member. The extension member extends into the iliac artery and forms a lumen for the flow of blood therethrough.

While the invention has been described with reference to particular embodiments, it will be understood to one skilled in the art that variations and modifications may be made in form and detail without departing from the spirit and scope of the invention.

What is claimed is:

1. An endoluminal prosthesis comprising:
   a tubular graft configured to sealingly engage an inner wall of a body lumen and comprising: a proximal portion comprising a trunk portion having a proximal opening, and a distal portion branched into a first branch portion and a second branch portion, each of the first and second branch portions having a distal opening, the trunk portion and the first and second branch portions forming a lumen for the flow of body fluids from the proximal opening through the distal openings of the first and second branch portions; and
   a valve located at least in part within the first branch portion, said valve comprising a first support member, a second support member and a section of graft material coupled to the first and second support members,
   wherein the first support member is coupled to the first branch portion within the first branch portion so that the first support member provides an opening in the first branch portion through which body fluids from the trunk portion may flow, and
   wherein the second support member has a first, closed position and a second, open position wherein in the first closed position a portion of the section of the graft material comprises a cover configured to prevent the flow of body fluids through the opening in the first branch portion, wherein the second support member is configured to hold the portion of the section of graft material in a position in which it is forms the cover, and wherein in the second, open position, the second support member is configured to hold the graft material in a position that permits the flow of body fluids through the opening in the first branch portion.

2. The endoluminal prosthesis of claim 1 wherein the first support member comprises an annular spring.

3. The endoluminal prosthesis of claim 2 wherein the graft material coupled to the annular spring forms a tube around the annular spring.

4. The endoluminal prosthesis of claim 1 wherein the second support member comprises a semicircular spring member.

5. The endoluminal prosthesis of claim 4 wherein the graft material forms a generally semicircular shape where it is coupled to the second support member.

6. The endoluminal prosthesis of claim 1 wherein the second support member comprises a spring member.

7. The endoluminal prosthesis of claim 1 wherein the first branch portion comprises an inner circumferential wall wherein in the closed position the second support member engages the inner circumferential wall.

8. The endoluminal prosthesis of claim 1 wherein the prosthesis is an aneurysm exclusion device.

9. The endoluminal prosthesis of claim 1 wherein the second support member comprises an annular member configured to fold into a semicircular member in the first, closed position and to open to a ring configuration in the second, open position.

10. An endoluminal prosthesis comprising:
    a tubular graft, configured to sealingly engage an inner wall of a body lumen and comprising: a proximal portion comprising a trunk portion having a proximal opening, and a distal portion branched into a first branch portion and a second branch portion, each of the first and second branch portions having a distal opening, the trunk portion and each of the first and second branch portions forming lumens for the flow of body fluids from the proximal opening through the distal openings of the at least two branch portions; and
    a valve located at least in part within the first branch portion, said valve comprising a support member comprising a portion of a ring and a section of graft material coupled to the support member, wherein the support member has a first, closed position and a second, open position wherein in the first closed position, the support member holds the graft material in a position that prevents flow of body fluids through the opening in the first branch portion, and wherein in the second, open position, the support member is engaged with the first branch portion so that the support member provides an opening in the first branch portion through which body fluids may flow from the tank portion through the distal opening in the first branch portion.

11. The endoluminal prosthesis of claim 10 wherein the first branch portion comprises an inner wall forming a branch lumen and wherein a portion the graft material of the support member is secured to the inner wall of the first branch portion.

12. The endoluminal prosthesis of claim 11
    wherein in the first, closed position, the support member is located within the branch lumen on the inner wall of the first branch portion at an opposite side of the branch lumen from the portion of the graft material secured to the inner wall of the first branch portion, and
    wherein in the second, open position, the support member is located adjacent the portion of the graft material secured to the inner wall of the first branch portion.

13. An endoluminal prosthesis comprising:
    a tubular graft configured to sealingly engage an inner wall of a body lumen and comprising: a proximal portion comprising a trunk portion having a proximal opening, and a distal portion branched into a first branch portion and a second branch portion, each of the first and second branch portions having a distal opening, the trunk portion and the first and second branch portions forming a lumen for the flow of body fluids from the proximal opening through the distal openings of the first and second branch portions; and
    a valve located at least in part within the first branch portion, said valve comprising:
       a section of graft material in the shape of a partial cylinder;
       a first support member comprising an annular member coupled to the section of graft material to form a lumen through the first support member and the section of graft material; and a second support member comprising a portion of an annular spring and coupled to the section of graft material, wherein the first support member is coupled to the first branch portion within the first branch portion so that the first support member provides said lumen through which body fluids from the trunk portion may flow, and wherein the second support member has a first, closed position within the tubular graft and a second, open position within the tubular graft wherein in the first, closed position a portion of the section of the graft material comprises a cover configured to prevent the flow of body fluids through the opening in the first branch portion, wherein the second support member is configured in a semi circular shape adjacent a first portion of the inner circumference of the tubular graft to hold the portion of the section of graft material in a position in which it is forms the cover, and wherein in the second, open position, the second support member is adjacent a second portion of the inner circumference of the tubular graft and is configured to hold the graft material in a position against the second portion of the inner circumference of the tubular graft to permit the flow of body fluids through the lumen.

14. An endoluminal prosthesis comprising:

a tubular graft means for sealingly engaging the inner wall of a body lumen and for excluding a portion of a body vessel, the tubular graft means including: a proximal portion comprising a trunk portion having a proximal opening, and a distal portion branched into at least two branch portions, each of the at least two branch portions having a distal opening, the trunk portion and the branch portions forming a lumen means for the flow of body fluids from the proximal opening through the distal openings of the at least two branch portions; and a valve means located at least in part within a first of the branch portions having a branch lumen means therethrough, said valve means comprising a graft means for providing a barrier to the flow of blood; and a first support means for opening and closing the valve means by covering or uncovering the branch lumen means to prevent or permit the flow of blood respectively from the trunk portion through the first of the branch portions.

15. The endoluminal prosthesis of claim 14 further comprising a second support means for providing an opening through the graft means in the first of the branch portions through which body fluids from the trunk portion may flow, wherein the first support means comprises means for opening and closing the opening provided by the second support means.

16. A method of deploying an endoluminal prosthesis comprising the steps of:

providing an endoluminal prosthesis comprising:
a tubular graft configured to sealingly engage an inner wall of a body lumen and comprising: a proximal portion comprising a trunk portion having a proximal opening, and a distal portion branched into a first branch portion and a second branch portion, each of the first and second branch portions having a distal opening, the trunk portion and the first and second branch portions forming a lumen for the flow of body fluids from the proximal opening through the distal openings of the first and second branch portions; and a valve located at least in part within the first branch portion, said valve a comprising a first support member, a second support member and a graft material coupled to the first and second support members, wherein the first support member is engaged with the first branch portion within the first branch portion so that the first support member provides an opening in the first branch portion through which body fluids from the trunk portion may flow, and wherein the second support member has a first, closed position and a second, open position wherein in the first closed position, the second support member holds the graft material in a position that prevents flow of body fluids through the opening in the first branch portion, and wherein in the second, open position, the second support member holds the graft material in a position that permits the flow of body fluids through the opening in the first branch portion;

locating a delivery catheter containing the endoluminal prosthesis at a site for deployment;

deploying the prosthesis at the site so that the prosthesis engages the inner wall of the body lumen wherein the valve is in a first closed position; and opening the valve.

17. The method of claim 16 wherein the step of opening the valve comprises:

providing an extension prosthesis loaded in a catheter;

locating the catheter in the first branch portion by positioning the distal end of the catheter through the valve to open the valve; and releasing the extension member so that a proximal portion of the extension member is located within the first branch portion and the distal end of the extension member is located within a branch artery.

18. The method of claim 17 wherein the first branch portion comprises an inner circumferential wall wherein in the closed position the second support member engages a first portion of the inner circumferential wall; and wherein the step of positioning the distal end of the catheter through the valve to open the valve comprises positioning the distal end of the catheter between the second support member and the first portion of the inner circumferential wall and moving the second support member away from its position against the first portion of the inner circumferential wall to a position against a second portion of the inner circumferential wall.

19. A method of deploying an endoluminal prosthesis comprising the steps of:

providing an endoluminal prosthesis comprising:
a tubular graft, configured to sealingly engage an inner wall of a body lumen and comprising a proximal portion comprising a trunk portion having a proximal opening, and a distal portion branched into a first branch portion and a second branch portion, each of the first and second branch portions having a distal opening, the trunk portion and each of the first and second branch portions forming lumens for the flow of body fluids from the proximal opening through the distal openings of the at least two branch portions; and a valve located at least in part within the first branch portion, said valve comprising a support member comprising a portion of a ring and a graft material coupled to the support member, wherein the support member has a first, closed position and a second, open position wherein in the first closed position, the support member holds the graft material in a position that prevents flow of body fluids through the opening in the first branch portion, and wherein in the second, open position, the support member is engaged with the first branch portion so that the support member provides an opening in the first branch portion through which body fluids may flow from the trunk portion through the distal opening in the first branch portion;

locating a delivery catheter containing the endoluminal prosthesis at a site for deployment;

deploying the prosthesis at the site so that the prosthesis engages the inner wall of the body lumen wherein the valve is in a first closed position; and opening the valve.

20. The method of claim 19 wherein the step of opening the valve comprises:

providing an extension prosthesis loaded in a catheter;

locating the catheter in the first branch portion by positioning the distal end of the catheter through the valve to open the valve; and releasing the extension member so that a proximal portion of the extension member is located within the first branch portion and the distal end of the extension member is located within a branch artery.

21. The method of claim 20 wherein the first branch portion comprises an inner circumferential wall wherein in the closed position the support member engages a first portion of the inner circumferential wall; and wherein the step of positioning the distal end of the catheter through the valve to open the valve comprises positioning the distal end of the catheter between the support member and the first portion of the inner circumferential wall and moving the support member away from its position against the first portion of the inner circumferential wall to a position against a second portion of the inner circumferential wall.

\* \* \* \* \*